US011285305B2

(12) United States Patent
Cinquin et al.

(10) Patent No.: US 11,285,305 B2
(45) Date of Patent: Mar. 29, 2022

(54) IMPLANTABLE DEVICE

(71) Applicants: UNIVERSITE GRENOBLE ALPES, Saint Martin d'Heres (FR); CENTRE HOSPITALIER UNIVERSITAIRE GRENOBLE ALPES, La Tronche (FR)

(72) Inventors: Philippe Cinquin, Saint Nazaire les Eymes (FR); Patrick Tuvignon, Albi (FR)

(73) Assignees: UNIVERSITE GRENOBLE ALPES, Saint Martin d'Heres (FR); CENTRE HOSPITALIER UNIVERSITAIRE GRENOBLE ALPES, La Tronche (FR)

( * ) Notice: Subject to any disclaimer, the term of this patent is extended or adjusted under 35 U.S.C. 154(b) by 71 days.

(21) Appl. No.: 16/467,354

(22) PCT Filed: Dec. 7, 2017

(86) PCT No.: PCT/EP2017/081905
§ 371 (c)(1),
(2) Date: Jun. 6, 2019

(87) PCT Pub. No.: WO2018/104481
PCT Pub. Date: Jun. 14, 2018

(65) Prior Publication Data
US 2019/0321612 A1    Oct. 24, 2019

(30) Foreign Application Priority Data
Dec. 7, 2016    (FR) ....................... 1662064

(51) Int. Cl.
*A61M 31/00*    (2006.01)
*A61M 25/00*    (2006.01)

(52) U.S. Cl.
CPC ... *A61M 31/002* (2013.01); *A61M 2025/0057* (2013.01); *A61M 2205/04* (2013.01);
(Continued)

(58) Field of Classification Search
CPC .......... A61M 31/002; A61M 2205/825; A61M 2025/0057; A61M 2205/04;
(Continued)

(56) References Cited

U.S. PATENT DOCUMENTS

| 6,361,780 B1 * | 3/2002 | Ley | ........................ A61M 31/00 424/400 |
| 2004/0147871 A1 * | 7/2004 | Burnett | ............. A61M 5/14276 604/9 |

(Continued)

FOREIGN PATENT DOCUMENTS

| EP | 1504778 A2 | 2/2005 |
| EP | 2515992 A2 * | 10/2012 ......... A61B 5/14539 |

(Continued)

OTHER PUBLICATIONS

International Search Report from corresponding International Application No. PCT/EP2017/081905, dated Jan. 17, 2018, pp. 1-6, European Patent Office, Rijswijk, The Netherlands.

(Continued)

*Primary Examiner* — Bhisma Mehta
*Assistant Examiner* — Neeraja Gollamudi
(74) *Attorney, Agent, or Firm* — Hauptman Ham, LLP

(57) ABSTRACT

The invention relates to an implantable device suitable for being fixed in a fixation position to a wall of a patient's stomach, the implantable device being accommodated in the stomach when the implantable device is in the fixation position, the implantable device being characterised in that it comprises a reserve of an active substance and an injector suitable for administering the active substance to the patient.

17 Claims, 4 Drawing Sheets

(52) U.S. Cl.
CPC . *A61M 2205/123* (2013.01); *A61M 2205/825* (2013.01); *A61M 2210/1017* (2013.01); *A61M 2210/1053* (2013.01); *A61M 2210/12* (2013.01); *A61M 2230/201* (2013.01)

(58) Field of Classification Search
CPC .... A61M 2205/123; A61M 2210/1017; A61M 2210/1053; A61M 2210/12; A61M 2230/201; A61M 5/14276; A61M 2205/3303; A61M 2210/1042
See application file for complete search history.

(56) References Cited

U.S. PATENT DOCUMENTS

| | | | |
|---|---|---|---|
| 2005/0038415 A1* | 2/2005 | Rohr | A23L 33/175 604/891.1 |
| 2008/0312712 A1* | 12/2008 | Penner | A61N 1/36007 607/40 |
| 2010/0076416 A1* | 3/2010 | Hoey | A61B 18/18 606/2 |
| 2010/0305664 A1* | 12/2010 | Wingeier | A61N 1/36007 607/62 |
| 2011/0144540 A1* | 6/2011 | Shen | A61M 5/16859 600/587 |
| 2012/0143021 A1* | 6/2012 | Nagar | A61M 5/1723 600/301 |
| 2012/0143029 A1* | 6/2012 | Silverstein | A61B 5/7475 600/374 |
| 2012/0283968 A1 | 11/2012 | Katsuki et al. | |
| 2013/0165772 A1* | 6/2013 | Traverso | A61M 31/002 600/431 |
| 2014/0180034 A1* | 6/2014 | Hoseit | A61B 5/0066 600/301 |
| 2014/0276546 A1* | 9/2014 | Connor | A61M 5/1723 604/503 |
| 2014/0288612 A1* | 9/2014 | Addington | A61B 5/113 607/41 |
| 2015/0374906 A1* | 12/2015 | Forsell | A61F 2/004 600/31 |
| 2016/0022180 A1 | 1/2016 | Joseph et al. | |
| 2016/0051806 A1* | 2/2016 | Goldsmith | A61N 1/00 604/21 |
| 2018/0311484 A1* | 11/2018 | Lake | A61M 25/1002 |

FOREIGN PATENT DOCUMENTS

| | | |
|---|---|---|
| GB | 2230781 A | 10/1990 |
| JP | 03-11059 | 1/1991 |
| JP | 2005-52656 | 3/2005 |
| JP | 2011-505988 | 3/2011 |
| WO | 02087657 A2 | 11/2002 |
| WO | 2006035446 A2 | 4/2006 |
| WO | 2009076547 A2 | 6/2009 |
| WO | WO-2011079302 A2 * | 6/2011 ............ A61M 31/00 |
| WO | 2011090003 A1 | 7/2011 |
| WO | 2011150032 A1 | 12/2011 |

OTHER PUBLICATIONS

Japanese Office Action issued in corresponding Japanese Application No. 2019530700, dated Aug. 30, 2021, pp. 1-5, Japanese Patent Office, Tokyo, Japan.

* cited by examiner

IMPLANTABLE DEVICE

FIELD

The present invention relates to an implantable device. The present invention also relates to a method for administering an active substance to a patient.

TECHNOLOGICAL BACKGROUND

Devices implanted in the body are used to administer medicinal products to patients. The implanted devices then comprise a battery and a medicinal product reserve. However, it is necessary to recharge or replace the batteries and reserves of such implantable devices regularly. In particular, in numerous cases, this replacement is carried out by means of a surgical procedure. Such a procedure is relatively expensive and restrictive for the patient since it takes place in a hospital facility operating theatre and anaesthesia is required, as well as a prolonged stay in the hospital facility for the purposes of post-operative monitoring. Furthermore, as for any surgical procedure, there are risks of the patient contracting an infection during the operation.

In other cases, implanted devices of the type mentioned above are externally powered by an energy storage module which is borne by the patient outside their body. For example, some power supply devices may transmit energy via ultrasound waves to the stimulation device, through the patient's skin and rib-cage. However, ultrasound waves pass poorly through bones, and great precision in the placement of the ultrasound source is then required, in cases where the implanted device is situated in front of the rib-cage, so as to provide a satisfactory power supply of the implanted device. Furthermore, such a power supply device outside the patient's body is unsightly.

Some implantable devices may be equipped with wired connectors, enabling an electrical connection or fluid transfer between the implantable device and an external device. In this way, an electrical power supply current or a flow of medicinal product are exchanged with the external device. Here again, these connectors emerging through the patient's skin are unsightly, and necessarily involve health risks as well as significant constraints for the patient's day-to-day life.

Therefore, there is a need for an implantable system that is less restrictive for the patient.

SUMMARY

For this purpose, there is proposed an implantable device suitable for being fixed in a fixation position to a wall of a patient's stomach, the implantable device being accommodated in the stomach when the implantable device is in the fixation position, the implantable device being characterised in that it comprises a reserve of an active substance and an injector suitable for administering the active substance to the patient.

According to the embodiments, the implantable device comprises one or a plurality of the following features, taken in isolation or according to any technically possible combinations:

the injector is configured to inject the active substance into a bodily fluid of the patient;

the bodily fluid is peritoneal fluid or blood;

the injector is configured to inject the active substance into the patient's digestive tract;

the injector includes at least one catheter suitable for enabling the injection of the active substance, by the injector, into a lumen of the patient's intestine;

the active substance is chosen from the set formed of insulin, levodopa, an analgesic and an anticancer drug;

the implantable device is suitable for being fixed in the upper part of the stomach;

the active substance reserve comprises a connector jointly connected to the injector and a capsule containing the active substance, the capsule being suitable for being swallowed by the patient and for connecting to the connector to deliver the active substance to the injector;

the implantable device comprises a sensor and at least one catheter suitable for directing a bodily fluid of the patient to the sensor, the sensor being suitable for measuring at least one value of a level of a biological marker in the bodily fluid;

the implantable device further comprises a controller suitable for commanding the administration, by the injector, of the active substance according to at least one measured level value;

the controller is suitable for computing a frequency and/or a dose of active substance to be administered to the patient according to at least one measured level value;

the bodily fluid is peritoneal fluid or blood;

the implantable device comprises an electrical power supply including a removable electrical energy reserve and a connector suitable for accommodating the electrical energy reserve, the electrical energy reserve being suitable for electrically powering the injector when the electrical energy reserve is connected electrically to the connector in a connection position and preferably being configured to be swallowed by the patient and to move spontaneously to the connection position from a disconnection position wherein the electrical energy reserve is accommodated in the stomach of the patient and is disconnected from the connector;

the implantable device comprises an electrical power supply suitable for generating an electrical power supply current of the injector by reacting at least one chemical species present in the patient's body, particularly glucose;

the implantable device comprises an electrical power supply suitable for generating an electrical power supply current of the injector by converting mechanical energy into electrical energy.

The implantable device may comprise two first catheters. The two first catheters may be connected, via the pump, to form a fluidic continuity. A first catheter may be connected to the intake of the pump, and the second to the discharge. Bodily fluid intake and discharge are carried out by the pump.

The invention also relates to a method for administering an active substance. This method particularly uses an implantable device as disclosed herein. It is to be noted that, in further examples, the implantable device is suitable for being implanted elsewhere than in the patient's stomach.

The method particularly comprises the use or fitting of such a device comprising one or two or more first catheters. The device is in position against the inner wall of the stomach, and the first catheter or, preferably, the two first catheters, traverse the wall of the stomach. The free end of the first catheter is placed in the organ or the cavity wherein the active substance is to be injected. The method comprises the injection or delivery of the active substance by this first catheter. In a preferred embodiment, two first catheters are used, the free end of a first catheter is placed in the organ or the cavity from which the bodily fluid is to be aspirated, whereas the free end of a second first catheter is placed in the organ or cavity wherein the active substance is to be injected. In one embodiment, said two ends are placed in the peritoneal space. In a further embodiment, said two ends are placed in the venous or arterial space. The method then comprises the creation of a flow of bodily fluid transiting via the two first catheters, from an intake end to a discharge end of this fluid. According to the method, the injection or delivery of the active substance is carried out in this flow of bodily fluid. The method comprises the use of the different modules of the device. Thus, the method comprises the control of the active substance injection flow rate, the continuous or fractionated injection, over a determined, controlled or monitored period of time. The method may thus comprise the measurement of a marker level and the command to administer the active substance. The method may also comprise the detection of the remaining level of active substance and trigger the change of active substance reserve. The method may also comprise the detection of the remaining level of electrical energy and trigger the change of energy reserve.

BRIEF DESCRIPTION OF THE FIGURES

Features and advantages of the invention will emerge on reading the following description, given merely by way of non-limiting example with reference to the appended drawings, wherein.

DETAILED DESCRIPTION

Figure 1:
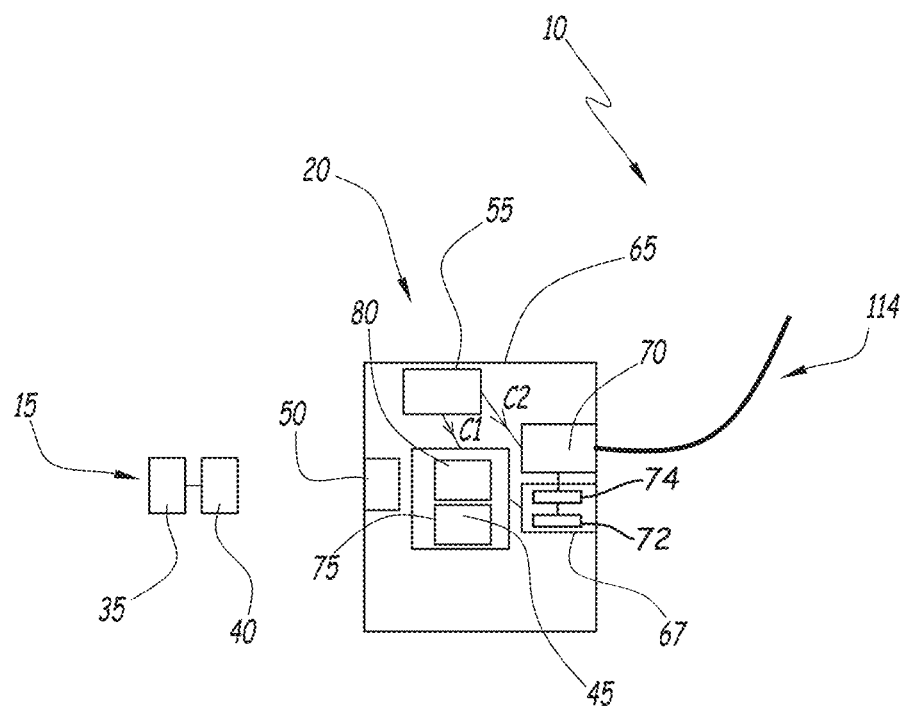
FIG. 1 is a diagram of an example of an implantable system including an electrical power supply.

A first example of an implantable system 10 is represented in FIG. 1.

The implantable system 10 includes an anchor 15 and an implantable device 20.

It is understood by "implantable system" that at least one element from the list formed by the anchor 15 and the implantable device 20 is envisaged to be implanted in the human body.

In particular, it is understood by "implantable" that at least one element from the anchor 15 and the implantable device 20 is envisaged to remain in the body of a patient P for a period strictly greater than one week, preferably greater than one month, preferably greater than or equal to one year.

Figure 2:
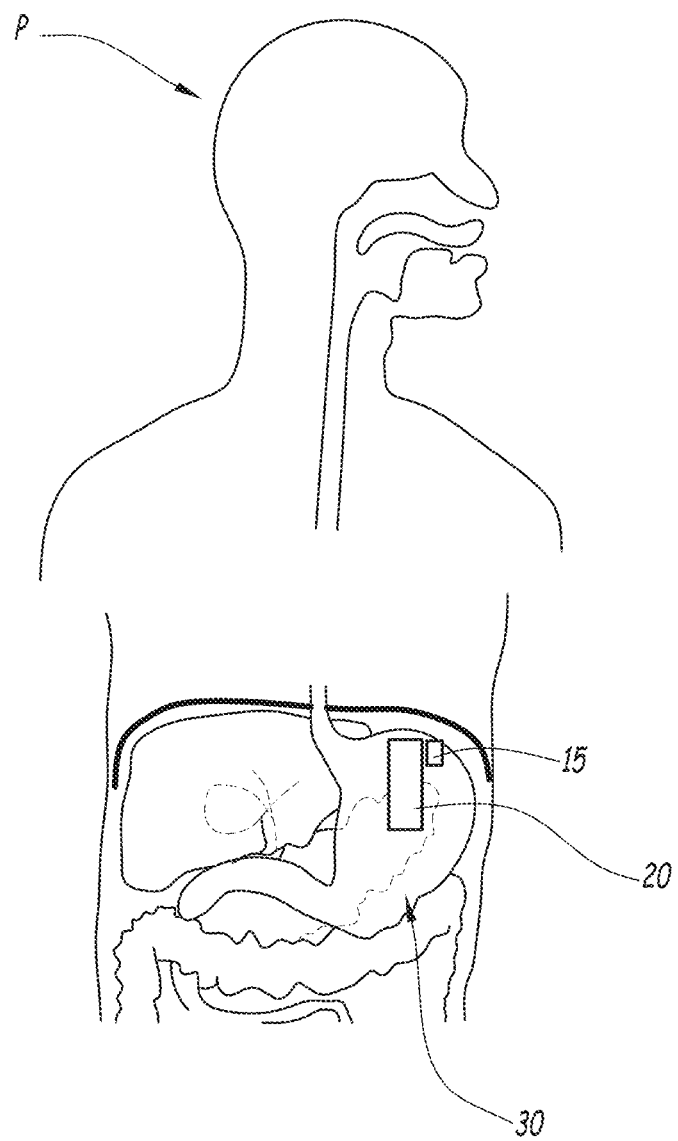
FIG. 2 is a schematic representation of the implantable device in FIG. 1, implanted in a patient's body.

The implantable system 10 has been represented schematically in FIG. 2 when the implantable system 10 is implanted in the body of the patient P.

According to the example in FIG. 2, the anchor 15 and the implantable device 20 are each implanted in the body of the patient P.

The anchor 15 is suitable for being fixed in a predetermined position in the stomach 30 of the patient P.

For example, the anchor 15 is configured to be fixed in the upper part of the stomach 30. In particular, the anchor 15 is configured to be fixed in the gastric fundus of the stomach 30. For example, the anchor 15 is envisaged to be fixed as close as possible to the angle of His in the gastric fundus.

Alternatively, the anchor 15 is configured to be fixed in the lower part of the stomach 30.

The anchor 15 is configured to support the implantable device 20, preferably removably. In particular, the anchor 15 and the implantable device 20 are configured to be fixed to one another, by a fixation device, and the anchor 15 is configured to hold the implantable device 20 in a fixation position when the anchor 15 is fixed in the stomach 30.

The anchor 15 includes a head 35 and a first connector 40.

The head 35 is configured to anchor the anchor 15 in the predetermined position. In particular, the head 35 is configured to anchor the anchor 15 to the wall of the stomach 30.

The head 35 is, for example, a gastrointestinal clip configured to grip between two branches of the head 35 a portion of the wall of the stomach 30.

Alternatively, the head 35 is suitable for being sutured using a suture to the wall of the stomach 30.

According to a further alternative embodiment, the head 35 is suitable for being embedded inside the gastric mucosa after the latter has been dissected.

The first connector 40 is configured to fix the implantable device 20 to the head 35.

The implantable device 20 is configured to administer an active substance to the patient P.

For example, the implantable device 20 is configured to inject an active substance into a bodily fluid of the patient P. The bodily fluid is, for example, the patient's peritoneal fluid (parenteral route). Alternatively, the bodily fluid is the blood of the patient P.

Alternatively, the implantable device 20 is configured to administer the active substance by the enteral route, particularly by releasing in the stomach.

"Active substance" denotes a substance having a favourable effect on the patient's health.

For example, a medicinal product is an active substance. A hormone is a further example of an active substance.

The active substance is, for example, insulin.

Alternatively, the active substance is an analgesic. For example, the active substance is morphine.

According to a further alternative embodiment, the active substance is levodopa. Levodopa, or L-dopa, is a medicinal product used in the treatment of Parkinson's disease.

According to a further alternative embodiment, the active substance is an anticancer drug. For example, the active substance is a chemotherapy component.

The implantable device 20 includes a first controller 45, a second connector 50, an electrical power supply 55, a housing 65, an active substance reserve 67 and an injector 70.

The first controller 45 is a data processing unit. The first controller 45 includes a first memory 75 and a first processor 80.

Alternatively, the first controller 45 is embodied in the form of a dedicated integrated circuit, or programmable logic components.

According to one embodiment, the first controller 45 includes a radiofrequency emitter/receiver.

A computer program containing program instructions is stored in the first memory 75. The program instructions are suitable, when executed by the first processor 80, for implementing a method for administering the active substance to the patient P.

The first processor 80 is suitable for processing and/or converting data represented as electronic or physical quantities in the first memory 75 into other similar data corresponding to physical data in the first memory 75, in registers or other types of display, transmission or storage devices.

The second connector 50 is configured to cooperate with the first connector 40 to hold the implantable device 20 in the fixation position.

For example, the second connector 50 is configured to cooperate with the first connector 40 by snap-fitting.

Alternatively, the second connector 50 includes a magnet configured to fix the second connector to the first connector. The magnet is, for example, an electromagnet.

According to a further alternative embodiment, the first connector 40 is configured to be secured to the second connector 50 by screwing. Alternatively, the first connector 40 includes one or preferably two bayonets complementary with fixation orifices formed in the second connector 50.

Preferably, the second connector 50 is envisaged such that the implantable device 20 is separable from the anchor 15. In particular, the second connector 50 is configured such that the implantable device 20 is separable from the anchor 15 when the anchor 15 is fixed in the stomach 30 of the patient P.

Figure 3:
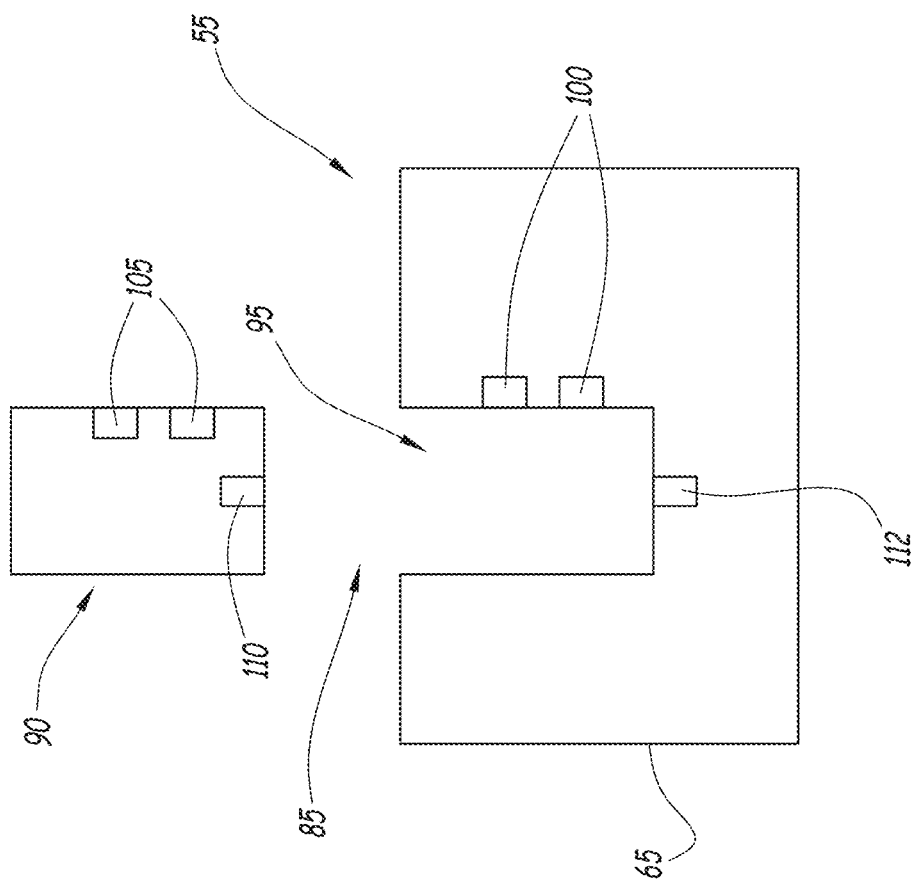
FIG. 3 is a schematic representation of the power supply in FIG. 1.

The electrical power supply 55 has been represented in FIG. 3.

The electrical power supply 55 is configured to supply the first controller 45 with a first power supply current C1.

The electrical power supply 55 is further configured to supply the injector 70 with a second power supply current C2.

The electrical power supply 55 includes a third connector 85 and a first electrical energy reserve 90.

The third connector 85 is configured to receive from the first electrical energy reserve 90 the first power supply current C1 and the second power supply current C2 and to supply the first controller 45 and the injector 70 with, respectively, the first power supply current C1 and the second power supply current C2.

The third connector 85 is configured to accommodate the first electrical energy reserve 90. In particular, the third connector 85 delimits a cavity 95 configured to accommodate at least partially the first electrical energy reserve 90 in a connection position.

According to the example in FIG. 3, the cavity 95 emerges outside of the housing 65. In particular, the cavity 95 is configured to enable the insertion of the first electrical energy reserve 90, from outside the housing 65, into the cavity 95.

The third connector 85 further includes two first electrical contacts 100, configured to be connected electrically to the first electrical energy reserve 90 when the first electrical energy reserve 90 is in the connection position. In particular, the two first electrical contacts 100 emerge inside the cavity 95.

The first electrical energy reserve 90 is configured to store electrical energy. In particular, the first electrical energy reserve 90 is configured to be charged with electrical energy outside the body of the patient P and to be discharged when the first electrical energy reserve 90 is in the connection position. For example, the first electrical energy reserve 90 includes a battery. Alternatively, the first electrical energy reserve 90 includes at least one capacitor or a supercapacitor.

The first electrical energy reserve is configured to supply the first controller 45 with the first power supply current C1 when the first electrical energy reserve 90 is in the connection position. Furthermore, the first electrical energy reserve 90 is configured to supply the injector 70 with the second power supply current C2 when the first electrical energy reserve 90 is in the connection position.

According to the example in FIG. 3, the first electrical energy reserve 90 includes two second electrical contacts 105 complementary with the first electrical contacts 100.

The first electrical energy reserve 90 may be envisaged to be swallowed by the patient P.

According to an alternative embodiment, the first energy reserve 90 is suitable for being replaced by endoscopy.

In particular, the first electrical energy reserve 90 has a volume strictly less than 6 millilitres (ml).

The first electrical energy reserve 90 further has three dimensions each measured along a respective direction, each direction being perpendicular to the two other directions, and each dimension is strictly less than 5 centimetres (cm).

The first electrical energy reserve 90 is movable between the connection position and a disconnection position. When the first electrical energy reserve 90 is in the disconnection position, the first electrical energy reserve 90 is accommodated in the stomach 30 of the patient P but is not connected electrically to the third connector 85. For example, when the first electrical energy reserve 90 is in the disconnection position, the first electrical energy reserve is fully removed from the cavity 95.

The first electrical energy reserve 90 is configured to move spontaneously from the disconnection position to the connection position. For example, the first electrical energy reserve 90 includes attractors 110.

The attractors 110 are configured to exert on the first electrical energy reserve 90, when the first electrical energy reserve 90 is in the disconnection position, a force tending to move the first electrical energy reserve 90 from the disconnection position to the connection position.

Furthermore, the attractors 110 are configured to hold the first electrical energy reserve 90 in the connection position.

The attractors 110 include, for example, a first magnet suitable for cooperating with a second magnet 112 of the third connector 85. Alternatively, the first magnet is suitable for cooperating with a ferromagnetic portion of the third connector 85. The first magnet and the second magnet 112 are, for example, electromagnets.

The housing 65 is configured to isolate the first controller 45 from outside the housing 65. For example, the housing 65 delimits a chamber accommodating at least the first controller 45 and the injector 70.

The active substance reserve 67 is configured to store the active substance and to send the active substance to the injector 70.

The active substance reserve 67 includes, for example, a connector 74 jointly connected to the housing 65 and a capsule 72 containing the active substance. The capsule is suitable for being swallowed by the patient P and for connecting to the connector to deliver the active substance to the injector. In particular, each capsule is configured to eject from the corresponding connector an empty capsule.

The injector 70 is suitable for injecting the active substance into an organ C of the patient P. For example, the injector 70 includes a pump and a first catheter 114.

The pump is configured to extract the active substance in the active substance reserve 67 and to send the active substance to the first catheter 114.

A peristaltic pump is an example of a pump suitable for being integrated into the injector 70.

The first catheter 114 has a first end and a second end. The first end is connected to the pump. The second end is suitable for administering to the patient P the active substance received from the pump.

When the bodily fluid F is peritoneal fluid, the second end emerges in the peritoneum, and the injector 70 is suitable for injecting the active substance in the peritoneal fluid of the patient P. The active substance may pass from the peritoneal fluid to the bloodstream of the patient P.

Alternatively, if the bodily fluid F is blood, the second end emerges into a blood vessel (vein or artery) of the patient P.

In the enteral alternative embodiment, the second end emerges in the digestive tract of the patient P. For example, the second end emerges in a lumen of the intestine of the patient P. Alternatively, the second end emerges in the stomach of the patient P.

The operation of the implantable system 10 will now be described.

During a first step prior to the implantation of the anchor 15, the implantable device 20 and the second device 25 in the body of the patient P, the first electrical energy reserve 90 is charged with electrical energy. The first electrical energy reserve 90 therefore generates the first power supply current C1 intended for the first controller 45.

During a second step, the anchor 15, the implantable device 20 and the second device 25 are implanted in the body of the patient P.

During a third step, an activation message is transmitted, by an external device, to the implantable device 20. In particular, the activation message is transmitted by radiofrequency communication. The activation message informs the first controller 45 that the implantable system 10 has indeed been implanted in the body of the patient P.

During a fourth step, the active substance is administered to the patient P.

The first controller 45 commands the administration of a quantity of active substance to the patient P, by the injector 70, with an administration frequency.

For example, the quantity of active substance administered and the administration frequency are predetermined.

The implantable device 20 makes it possible to deliver active substances, either enterally, or parenterally. The implantable device 20 therefore makes it possible to deliver simply and painlessly for the patient P active substances that are usually injected, for example by the intravenous or intramuscular route.

The implantable device 20 also makes it possible to deliver active substances automatically and regularly, for example in the case where arrival into the intestine must take place at as constant a flow rate as possible, such as L-Dopa for certain Parkinson's patients. By means of the device 20, administration of the active substance is facilitated. Indeed, the capsule containing the active substance may be administered to the patient per os, which is therefore not very painful and not very restrictive for the patient. In particular, the number of capsules of active substance to be swallowed is much less than the number of doses of medicinal product to be administered, over the same period, to arrive at the same administrate rate if the medicinal products are administered in conventional pill form.

Furthermore, the implantable device 20, once fitted, is not very restrictive for the patient P. In particular, the implantable device 20 is suitable for replacing external infusions, but does not represent like these an impediment to the patient's movement.

Given that the implantable device 20 is in the stomach, the replacement of the first electrical energy reserve 90 is easy and may, for example, be carried out endoscopically via the oesophagus, simply and quickly. Furthermore, the replacement of the first electrical energy reserve 90 involves few risks of infection since no incision is made.

The use of the attractors 110 renders the positioning of the first electrical energy reserve 90 even simpler, even without endoscopy, since it is simply necessary for the patient P to swallow the first electrical energy reserve 90.

Furthermore, the implantable system 10 does not mean that the patient P continuously bears electrical energy storage means outside their body, or that unsightly electrical conductors emerge out of the body of the patient P. The implantable system 10 therefore involves few constraints for the patient.

A second example of an implantable system 10 will now be described. Identical elements to the first example of an implantable system 10 in FIG. 1 are not described again. Only the differences are highlighted.

Figure 4:
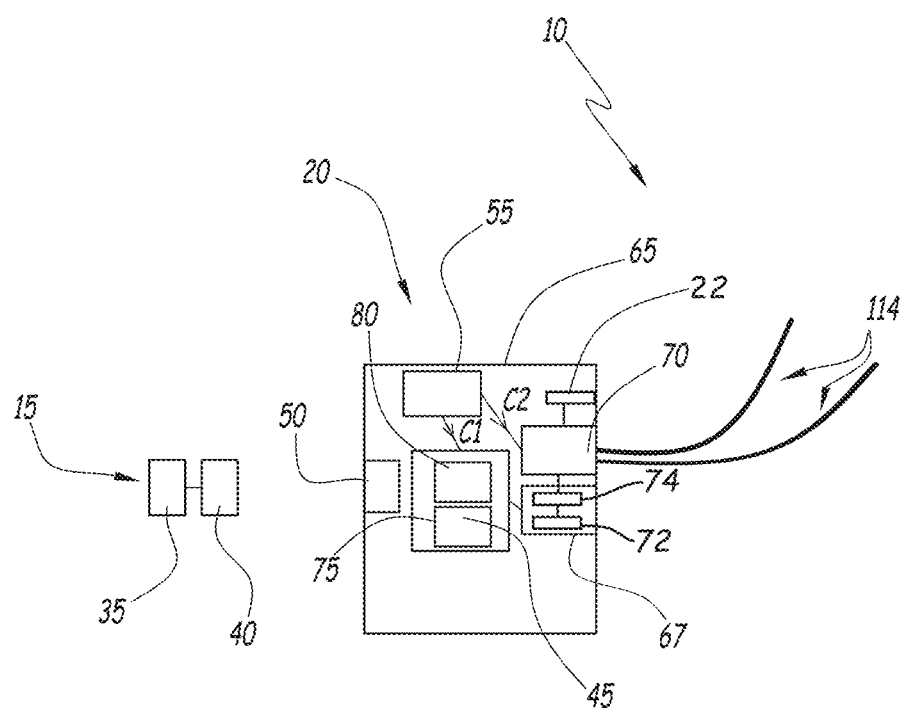
FIG. 4 is a diagram of another example of an implantable system.

As shown in FIG. 4, the implantable device 20 includes at least one sensor 22. Each sensor is suitable for measuring a value of a representative parameter of a physiological phenomenon of the patient P.

A parameter is, for example, a level of a biological marker in a bodily fluid F of the patient P.

The implantable device 20 then includes a second catheter configured to direct a bodily fluid F from the patient P from the organ C to the sensor. For example, the organ C is the peritoneum, and the fluid F is peritoneal fluid.

The biological marker is, for example, glucose.

Alternatively, the biological marker is an ion present in the bodily fluid F.

The sensor is then suitable for measuring a level of the biological marker in the bodily fluid F. For example, the sensor is suitable for measuring a glucose level.

The first controller 45 is configured to command the injection of the active substance, by the injector 70, according to at least one measured parameter value. The first controller 45 is suitable for modifying an administration period or frequency of the active substance and/or a dose of active substance to be administered to the patient according to the values measured.

For example, the sensor measures values of the parameter with a predetermined measurement period, and the first controller 45 commands the administration of the active substance, by the injector 70, according to the values measured.

For example, the first controller 45 compares the values of the parameters measured to a predetermined threshold and commands the administration of a dose of active substance if one or a plurality of values measured are greater than or equal to the predetermined threshold. The dose of active substance administered is, for example, a dose corresponding to a predetermined volume.

Alternatively, the first controller 45 commands the administration of a dose of active substance with a predetermined administration period, each dose administered corresponding to a volume of active substance computed according to the values measured.

According to one alternative embodiment of the second example, the sensor is separate from the implantable device 20. For example, the implantable system 10 comprises an additional device suitable for being implanted in the body of the patient P and for communicating by radiofrequency communication with the implantable device 20.

The sensor is then integrated in the additional device. For example, the additional device is configured to send the values measured to the implantable device 20 by radiofrequency communication.

In this case, the additional device comprises a second controller including a second memory and a second processor and suitable for commanding the acquisition of values of the parameter by the sensor as well as the sending of radiofrequency transmission messages of the values measured to the implantable device 20.

A third example of an implantable system 10 will now be described. Identical elements to the first example of an implantable system 10 are not described again. Only the differences are highlighted.

The electrical power supply 55 does not include a third connector 85 or electrical energy reserve 90.

The electrical power supply 55 includes an electrical energy generator. It is understood by "electrical energy generator" that the electrical energy generator is not configured to be charged with electrical energy by an electric current.

The electrical energy generator is suitable for generating at least one electric current by reacting at least one chemical species present in the body of the patient P. More specifically, the electrical energy generator is suitable for generating the first power supply current C1 and the second power supply current C2.

For example, the electrical energy generator comprises two electrodes, the electrodes being immersed in the gastric juices of the patient P when the centralisation device 20 is in the fixation position. Alternatively, the electrodes of the electrical energy generator are envisaged to be immersed in the intestine of the patient P when the centralisation device 20 is in the fixation position.

Each electrode includes at least one enzyme. Alternatively, each electrode includes at least one microorganism. For example, each electrode of the electrical energy generator includes an electrical conductor coated with the enzyme or microorganism, the whole thus formed being surrounded by a membrane. The membrane is, for example, configured to be traversed by certain chemical species naturally present in the stomach of the intestine of the patient P.

When the electrodes of the electrical energy generator are immersed in the gastric juices or in the intestinal fluid, one of the electrodes acts as an anode in an oxidation-reduction reaction involving a first chemical species. At the same time, the other electrode acts as a cathode in an oxidation-reduction reaction involving a second chemical species.

By the simultaneous oxidation and reduction of the first chemical species and the second chemical species, an electrical voltage appears between the two electrical conductors. The first power supply current C1 and the second power supply current C2 are then generated.

The first chemical species is, for example, glucose. The second chemical species is, for example, oxygen.

The first chemical species is, for example, glucose. The second chemical species is, for example, oxygen.

The third example of an implantable system 10 does not require electrical charging of an electrical energy reserve 90 or insertion of the electrical energy reserve 90 in the body of the patient P.

The constraints for the patient P are, here again, reduced.

According to a fourth example, the electrical energy generator is suitable for generating at least one electric current by converting mechanical energy into electrical energy. In particular, the electrical energy generator is suitable for generating at least one electric current from the movements of the stomach 30.

In the above description, the functions of the implantable system 10 have been separated into several examples to facilitate the comprehension thereof by the reader. However, it is to be noted that the preceding examples may be combined to give rise to new embodiments.

Furthermore, the above description has been given in the case wherein the anchor 15 and the implantable device 20 form two separate devices. Those skilled in the art will readily understand that the implantable device 20 and the anchor 15 are suitable for forming a single device, the anchor 15 and the implantable device 20 then not being separable from one another. For example, the anchor 15 is integral with the housing 65 of the implantable device 20.

A fifth example of an implantable system 10 will now be described. Identical elements to the first example of an implantable system 10 are not described again. Only the differences are highlighted.

According to a fifth example of an implantable device 20 as shown in FIG. 4, the injector 70 includes two first catheters 114.

The pump is, for example, configured to aspirate via a first catheter 114 a bodily fluid F, and to discharge via the other catheter 114 the aspirated bodily fluid F. According to one embodiment, the pump is further configured to inject the active substance into the bodily fluid F such that the discharged fluid F is charged with the active substance.

According to one embodiment, each first catheter 114 traverses the wall of the stomach 30 to emerge between the parietal layer and the visceral layer of the peritoneum. In particular, the second end of each first catheter 114 emerges between the parietal layer and the visceral layer of the peritoneum.

The length and/or the diameter of the first catheters according to the invention is generally adapted to the location of the site of collection of the bodily fluid and/or discharge of this fluid after passing in the pump. When the bodily fluid F is peritoneal fluid, for example (but not exclusively), each first catheter 114 may particularly have a length between 1 centimetre (cm) and 20 cm, for example between 2 cm and 15 cm, in particular between 6 cm and 12 cm. Each first catheter 114 may have a diameter less than or equal to 3 millimetres (mm), for example less than or equal to 2 mm.

According to one embodiment, if the implantable device 20 includes two first catheters 114, one of the first catheters 114 acts as a second catheter.

An administration method implemented using an implantable device 20 according to the fifth example will now be described.

The administration method includes an intake step, an injection step and an expulsion step.

During the intake step, a flow of bodily fluid F is aspirated by one of the first catheters 114. For example, the first controller 45 commands the intake of the bodily fluid F via the pump.

During the injection step, a dose of the active substance is injected by the pump into the flow of bodily fluid F. For example, the first controller 45 commands the injection by the pump of the active substance into the flow of bodily fluid F.

During the expulsion step, the bodily fluid F containing the active substance is discharged by the other first catheter 114. In particular, the bodily fluid F containing the active substance is discharged into the same organ or the same cavity of the patient P wherefrom the bodily fluid F was aspirated. The active substance is therefore thus administered in the bodily fluid F of the patient P.

According to one embodiment, the two first catheters 114 emerge in the peritoneum, for example between the visceral layer and the parietal layer of the peritoneum. The bodily fluid F is then the peritoneal fluid.

It is to be noted that the two first catheters 114 are suitable for emerging in other organs of the patient P. For example, the two first catheters 114 each emerge in a blood vessel of the patient P. The bodily fluid F is then blood.

The intake, injection and expulsion steps have been described hereinafter as separate steps. However, these three steps are suitable for being carried out simultaneously. For example, a continuous flow of the bodily fluid F is aspirated by one of the first catheters 114, receives the active substance and is discharged by the other first catheter 114.

According to one embodiment, the intake, injection and expulsion steps are carried out continuously over a prolonged period of time, for example a period of time greater than or equal to one hour, greater than or equal to one day, or greater than or equal to one week.

According to a further embodiment, the intake, injection and expulsion steps are carried out in a fractionated manner, in particular with a frequency determined by the first controller 45. The frequency is, for example, determined by the first controller 45 based on the values of the parameter measured by the sensor.

During an optional cleaning step, a flow of bodily fluid F is aspirated by one of the first catheters 114 and discharged by the other first catheter 114 without an active substance active being injected into the bodily fluid F. The flow of bodily fluid then expels from the first catheter 114 whereby the flow is discharged particles, agglomerates and other solid elements, liable to have entered, or been formed, in the lumen of the first catheter 114. This step is, for example, subsequently repeated by inverting the first catheter 114 whereby the flow is discharged and the first catheter 114 whereby the flow is aspirated.

According to one alternative embodiment, the cleaning step comprises the injection via each first catheter 114 of an enzyme suitable for dissolving fibrinous formations or clots liable to have been formed in the catheter(s) 114. Urokinase and streptokinase are examples of enzymes.

The enzyme injection is, for example, carried out at least once per month, for example at least once per week. According to one embodiment, the enzyme injection is carried out once per day.

The enzyme is, in particular, stored in an enzyme reserve integrated in the implantable device 20.

When the injection of active substance takes place via a flow of bodily fluid F aspirated by one first catheter 114 and discharged by the other first catheter 114, the discharge of the active substance from the first catheter 114 is facilitated by the flow of bodily fluid F. In particular, all of the active substance injected by the pump is effectively discharged from the first catheter 114 even if the quantity of active substance is very small and would otherwise be liable to remain partially inside the first catheter, or if the bodily fluid F wherein the active substance is discharged exerts a pressure suitable for preventing the active substance active from coming out of the first catheter 114.

The regulation of the injection is therefore more effective, since very small quantities of active substance may be administered to the patient with great precision. In particular, it can be envisaged to distribute the administration over time, by administering very small doses of active substance multiple times or based on a continuous release over a determined duration. This arrangement of the invention indeed enables advantageous regulated dilution of the active substance.

The doses of active substance administered being very small, the side-effects for the patient P are suitable for being reduced with respect to an administration of larger doses with a lower frequency.

Furthermore, the flow of bodily fluid F discharged by the first catheter 114 makes it possible to unblock a first catheter 114 liable to have been partially or completely blocked, during the active substance injection step or a cleaning step.

Each first catheter 114 is made of a biocompatible material. The biocompatible material is for example chosen among polyurethanes, silicone, nylons, polycarbonate resins or polysulphones.

Each first catheter 114 is, for example, made of a porous material. In particular, the porous material is configured to be traversed at least by the active substance. According to one embodiment, the porous material is configured to be traversed by the active substance and by the bodily fluid F.

Polyvinyl alcohol (also known as PVA) is an example of porous material suitable for forming a first catheter 114.

According to one alternative embodiment, the porous material is a naturally non-porous material but wherein perforations have been formed. The perforations then act as pores.

Embodiments wherein the second end is open, i.e. where the central lumen of the first catheter 114 emerges outside the first catheter 114 may be envisaged, as may embodiments wherein the second end is closed.

When the first catheter(s) 114 are made of a porous material, the bodily fluid F is aspirated in part via the second end and in part via the pores or perforations of the porous material. Similarly, the active substance, and if applicable the bodily fluid F are aspirated in part via the second end and in part via the pores or perforations of the porous material.

When the second end of each first catheter 114 is closed, the active substance, and if applicable the bodily fluid F, are exchanged between the first catheter 114 and the body of the patient via the pores or perforations of the first catheter 114.

The choice of a porous material for the first catheter(s) 114 enables an intake and/or expulsion of fluid via the pores, over the entire length of the first catheter 114 in question. The first catheter(s) 114 are then less sensitive to any obstruction of the lumen of the catheter. Furthermore, the active substance is distributed in a larger zone of the body of the patient P than if the active substance were expelled merely via the second end. Any side-effects dependent on the volume density of active substance are therefore limited.

According to one embodiment, each first catheter 114 includes a bearing element suitable for bearing against the outer wall of the stomach 30 or against the visceral layer of the peritoneum. The bearing element is, for example, configured to, when bearing against the outer wall of the stomach 30 or against the visceral layer of the peritoneum, exert a force tending to move the implantable device 20 closer to the inner wall of the stomach 30, in particular to press the implantable device 20 against the inner wall of the stomach 30.

In this example, the first catheter(s) 114 act as an anchor 15 for fixing the implantable device 20 to the wall of the stomach 30.

According to one embodiment, each first catheter 114 is fixed to the stomach wall by means of sutures traversing collectively the wall of the stomach 30 and the first catheter 114. In this case, each first catheter 114 bears, for example, at least one strand or tie suitable for being fixed to the wall of the stomach 30.

According to a further example, the implantable device 20 is at least partially integrated inside the stomach mucosa. For example, the implantable device 20 is placed between the stomach mucosa and the muscularis of the stomach. According to one positioning mode, the implantable device 20 is placed between the stomach mucosa and the stomach submucosa.

According to a further example, the head 35 includes at least one base situated outside the stomach 30. For example, the head 35 includes two bases.

Each base is configured to bear against the outer face of the wall of the stomach 30 and to be connected to the implantable device 20 so as to exert a force tending to press the implantable device 20 against the inner face of the wall of the stomach 30. According to an alternative embodiment, each base is configured to be placed between the visceral layer and the parietal layer of the peritoneum and to bear against the visceral layer to press the implantable device 20 against the inner face of the wall of the stomach 30.

Each base is, for example, a plate. Alternatively, each base includes a lattice of strands stretched on a frame, in particular a flexible frame suitable for being bent and inserted into to an endoscope or a hollow needle.

The first connector 40 includes, for example, one or a plurality of rings jointly connected to the housing 65. Each base is, for example, fixed to the implantable device 20 by one or a plurality of strands fixed to one or a plurality of rings.

Fixation by one or a plurality of bases makes it possible to distribute the pressure exerted by the implantable device over a larger surface of the wall of the stomach 30 and therefore decrease the force exerted. Furthermore, this fixation mode does not imply generating in the stomach wall a fold reducing the volume of the stomach, which is liable to give rise to tensions in the anchor fixed thereto. Since the forces exerted on the stomach wall are reduced, the risks of onset of an inflammatory reaction of the gastric mucosa are limited.

The invention claimed is:

1. An implantable device suitable for being fixed in a fixation position to a wall of the stomach of a patient, the implantable device being accommodated in the stomach when the implantable device is in the fixation position,
the implantable device comprising a reserve of an active substance and an injector suitable for administering the active substance to the patient,
wherein
the injector is configured to inject the active substance into a bodily fluid of the patient,
the injector includes two catheters, the injector being configured to administer the active substance to the patient via at least one of the two catheters,
the injector is configured to aspirate, via one of the two catheters, the bodily fluid of the patient and to discharge, via the other catheter of the two catheters, the aspirated bodily fluid, and
the active substance is chosen from a set formed of: insulin, levodopa, an analgesic and an anticancer drug.

2. The implantable device according to claim 1, wherein the bodily fluid is peritoneal fluid or blood.

3. The implantable device according to claim 1, wherein the implantable device comprises a sensor and at least one of the two catheters suitable for directing the bodily fluid of the patient to the sensor, the sensor being suitable for measuring at least one value of a level of a biological marker in the bodily fluid.

4. The implantable device according to claim 3, further comprising a controller suitable for commanding the administration, by the injector, of the active substance according to the at least one measured value of the level of the biological marker.

5. The implantable device according to claim 4, wherein the controller is suitable for computing a frequency and/or a dose of active substance to be administered to the patient according to the at least one measured value of the level of the biological marker.

6. The implantable device according to claim 3, wherein the bodily fluid is peritoneal fluid or blood.

7. The implantable device according to claim 1, wherein the implantable device comprises an electrical power supply including a removable electrical energy reserve and a connector suitable for accommodating the electrical energy reserve, the electrical energy reserve being suitable for electrically powering the injector when the electrical energy reserve is connected electrically to the connector in a connection position.

8. The implantable device according to claim 1, wherein the implantable device comprises an electrical power supply suitable for generating an electrical power supply current of the injector by reacting at least one chemical species present in the body of the patient.

9. The implantable device according to claim 1, wherein the implantable device comprises an electrical power supply suitable for generating an electrical power supply current of the injector by converting mechanical energy into electrical energy.

10. The implantable device according to claim 1, wherein the injector is configured to inject the active substance into the discharged bodily fluid.

11. The implantable device according to claim 1, wherein at least one of the two catheters is made of a porous material.

12. The implantable device according to claim 11, wherein the porous material is suitable for being traversed by the active substance and/or by the bodily fluid of the patient.

13. A method for administering an active substance to a patient utilizing an implantable device suitable for being fixed in a fixation position to a wall of the stomach of the patient, the implantable device being accommodated in the stomach when the implantable device is in the fixation position, the implantable device including a reserve of the active substance and an injector suitable for administering the active substance to the patient,
wherein,
the injector is configured to inject the active substance into a bodily fluid of the patient,
the injector includes two catheters, the injector being configured to administer the active substance to the patient via at least one of the two catheters, and
the two catheters include a first catheter and a second catheter, a free end of the first catheter being placed in an organ or a cavity from which a bodily fluid is to be aspirated, and a free end of the second catheter being placed in an organ or a cavity wherein the active substance is to be injected,
the method comprising:
creating a flow of bodily fluid transiting via the first and second catheters, from an intake end to a discharge end, enabling the injection of the active substance in the flow of bodily fluid,
wherein the injector aspirates, via one of the two catheters, the bodily fluid of the patient and discharges, via the other catheter of the two catheters, the aspirated bodily fluid, and
the active substance is chosen from a set formed of: insulin, levodopa, an analgesic and an anticancer drug.

14. The method according to claim 13, further comprising:
positioning the implantable device against the wall of the stomach, wherein the second catheter traverses the wall of the stomach, and
injecting the active substance via the second catheter.

15. The method according to claim 13, wherein, the implantable device further comprises a sensor and at least one catheter of the first and second catheters suitable for directing the bodily fluid of the patient to the sensor, the sensor being suitable for measuring at least one value of a level of a biological marker in the bodily fluid, and the method further comprises measuring the level of the biological marker and commanding administration of the active substance.

16. The method according to claim 15, wherein, the implantable device further comprises a controller suitable for commanding the administration, by the injector, of the active substance according to the at least one measured value of the level of the biological marker, the method further comprises controlling an active substance injection flow rate, over a determined, controlled or monitored period of time.

17. The method according to claim 16, wherein, the implantable device further comprises an electrical power supply including a removable electrical energy reserve and a connector suitable for accommodating the electrical energy reserve, the electrical energy reserve being suitable for electrically powering the injector when the electrical energy reserve is connected electrically to the connector in a connection position, and the method further comprises detecting a remaining level of electrical energy of the implantable device and triggering a change of energy reserve.

* * * * *